United States Patent
Yuntao et al.

(10) Patent No.: US 9,702,814 B2
(45) Date of Patent: *Jul. 11, 2017

(54) SYSTEMS AND METHODS OF INFRARED DETECTION OF COAL MINE POLAR GAS

(71) Applicant: CCTEG (China Coal Technology and Engineering Group Corp), Beijing (CN)

(72) Inventors: Liang Yuntao, Fushun (CN); Sun Yong, Fushun (CN); Luo Haizhu, Fushun (CN); Zhang Depeng, Fushun (CN); Feng Wenbin, Fushun (CN); Fuchao Tian, Fushun (CN); Haozhe Dong, Shenzhen (CN); Hongli Fan, Fushun (CN)

(73) Assignee: CCTEG (China Coal Technology and Engineering Group Corp), Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/392,614

(22) Filed: Dec. 28, 2016

(65) Prior Publication Data

US 2017/0108432 A1 Apr. 20, 2017

Related U.S. Application Data

(62) Division of application No. 14/815,490, filed on Jul. 31, 2015.

(30) Foreign Application Priority Data

Jul. 31, 2014 (CN) .......................... 2014 1 0371238

(51) Int. Cl.
*G01N 21/3504* (2014.01)
*G01N 21/01* (2006.01)
*G01N 33/00* (2006.01)

(52) U.S. Cl.
CPC ......... *G01N 21/3504* (2013.01); *G01N 21/01* (2013.01); *G01N 33/0057* (2013.01); *G01N 2021/0193* (2013.01)

(58) Field of Classification Search
CPC ............... G01N 21/3504; G01N 21/11; G01N 2021/036; G01N 2021/0389
See application file for complete search history.

(56) References Cited

U.S. PATENT DOCUMENTS 5,708,273 A * 1/1998 VonBargen ........ G01N 21/8507
250/339.11

FOREIGN PATENT DOCUMENTS

WO WO 2005111580 A1 * 11/2005 ........ B01L 3/502715

* cited by examiner

*Primary Examiner* — Casey Bryant

(57) ABSTRACT

An infrared detection device can be used to detect coal mine polar gas. The detection device can include a central processor and a gas pool assembly having a moveable optical window. The moveable optical window can include a stationary pool body and a moveable pool body inserted into the stationary pool body.

20 Claims, 8 Drawing Sheets

SYSTEMS AND METHODS OF INFRARED DETECTION OF COAL MINE POLAR GAS

CROSS-REFERENCE TO RELATED APPLICATIONS

This application claims the benefit of U.S. Non-provisional patent application Ser. No. 14/815,490; filed Jul. 31, 2015; and entitled SYSTEMS AND METHODS OF INFRARED DETECTION OF COAL MINE POLAR GAS; the entire contents of which are incorporated herein by reference. U.S. Non-provisional patent application Ser. No. 14/815,490 claims the benefit of Chinese Patent Application No. 201410371238.5; filed Jul. 31, 2014; and entitled INFRARED DETECTION DEVICE FOR COAL MINE POLAR GAS AND DETECTION METHOD; the entire contents of which are incorporated herein by reference.

BACKGROUND

Field

The present invention relates to an infrared spectrum analysis technology and device for gas, more particularly, relates to an infrared detection device for coal mine polar gas and a detection method for the same.

Description of Related Art

Different oxidation stages of spontaneous combustion of coal correspond to different auto-ignition temperature ranges, different kinds and concentrations of gas products. The gas products for forecasting and predicting the spontaneous combustion process typically include CO, CO2, CH4, C2H6, C3H8, C4H10, C2H4, C3H6, C2H2, and the like. The spontaneous combustion of coal can be precisely forecasted according to constitution, concentration, changing rate and other characteristics of the oxidized gas products, which can allow a coal mine to be fire-proofed for safe production of work. The indications for detecting spontaneous combustion mainly include the indication of CO and derivative thereof, the indication of alkene-alkane ratio, the indication of alkyne gas, the indication of alkane ratio and the like.

During the management and reuse of a mine closed for a fire, the composition of the gas in the fire site should be monitored. At this time the monitored gases mainly comprise CO, $C_2H_2$, $C_2H_4$. However, after a gas explosion at a coal mine, the main noxious gases comprise CO, $C_2H_4$, $C_2H_6$ and the like. Thus, during the production of coal, in order to prevent the spontaneous combustion of coal and the gas explosion of the coal mine whether in the daily production of coal or in the emergency and rescue after the disaster, the above-mentioned gas should be analyzed quickly and precisely.

Current gas detection methods for the coal mine industry comprise a sensor-based method and a gas chromatography. The sensor-based method is impacted by downhole conditions and the detection result thereof thus has relatively large error. For instance, in case of low concentration of oxygen, a methane sensor equipped in a present portal explosion measuring instrument will produce a result with relatively large deviation. As for the gas chromatography, different components of the gas to be detected have to be adsorbed to and desorbed from a chromatographic column at different time periods, thus the whole analysis may take a long time such that a timely analysis cannot be achieved. Meanwhile the chromatographic column in the chromatographic analysis device may require frequent maintenance. Furthermore, the procedure of the chromatographic analysis system generally has to test a sample first each time, thus the technology is quite complicated and the analysis result will vary from person to person due to the different levels of technical skill.

An infrared spectrum analyzer may analyze the gas with the help of a gas pool. Since impacted by the structure of the gas pool, background gas inside the pool cannot be completely discharged, which may have an adverse impact on the test result. When gas concentration is monitored by being sampled continuously, this impact will be moderated by blowing gas over a longer period of time. However, the interference gas eventually cannot be thoroughly discharged. With regard to the investigation of fire accidents at coal mines, the gas to be analyzed is gathered by a person downhole of the coal mine. However, the interference of background gas inside the pool may only be eliminated by the person through gas blowing. As well, the gas inside the gas pool may be very hard to be substituted by the gas to be analyzed, which may produce a great impact on the accuracy of the gas quantificational analysis result of the infrared spectrum method.

Recently, as for the infrared detection device for coal mine polar gas and a detection method for the same, the detection device may comprise Bruker Tensor 27, Bruker ALPHA made in Germany, and Perkin Elmer Spectrum 100 made in the USA. The above-mentioned devices may both comprise a central processor, which can be electrically connected to a power supply, a light source, a detector, an alarm and indication lamp, an input and output module, a data collection and storage module. The power supply may also be electrically connected to a power supply switch and a power supply interface. The input and output module may also be connected to a computer communication interface. The data collection and storage module may also be electrically connected to the detector. As well, a detachable gas pool with a gas inlet and a gas outlet may be provided between the light source and the detector. The method for this infrared detection device for coal mine polar gas with such structure may comprise the following steps: firstly detaching the gas pool during the gas detection and filling $N_2$ gas of 99.999% content into the gas pool from the gas inlet; after replacing the gas in the gas pool, closing the gas outlet firstly and closing the gas inlet until the pressure is balanced; putting back the gas pool; scanning the spectrogram of the background gas until there is no gas peak value; during the hand sampling, connecting the gas bag filled with the gas to be detected to the gas inlet, opening the gas inlet valve and then opening the gas outlet valve; pressing the gas to be detected into the gas pool until the $N_2$ is completely discharged, closing the gas outlet valve and then the gas inlet valve; scanning the spectrogram of the gas to be detected so as to analyze the gas to be detected. Since there are blind angles at both ends inside the gas pool, the background air cannot be thoroughly replaced by $N_2$ and then $N_2$ cannot be thoroughly discharged, which render the spectrum of the gas to be detected distorted and the analysis of the gas to be detected inaccurate, thus, there are some risks of causing safety misadventure at the coal mine. Furthermore, in the method for this infrared detection device for coal mine polar gas with such structure, the gas pool has to be detached and is complicated to be used. Thus, there is a need for devices and methods to analyze the above-mentioned gases in an effort to ensure continuous production within a mine and safety of mine workers.

SUMMARY

The present application discloses detection devices and methods to overcome or alleviate at least one aspect of the above mentioned disadvantages in the current infrared detection device for coal mine polar gas. The disclosure includes an infrared detection device for detecting coal mine polar gas, comprising: a central processor disposed with an outer casing, the central processor being electrically connected to a power supply, a light source, a detector, an alarm and indication lamp, an input and output module, a data collection and storage module, the power supply also being electrically connected to a power supply switch and a power supply interface, the input and output module also being connected to a computer communication interface, and the data collection and storage module also being electrically connected to the detector, and a gas pool assembly having a moveable optical window and fixed on the device is provided between the light source and the detector.

In some embodiments, the gas pool assembly having a moveable optical window can include: a stationary pool body having a gas inlet with a gas inlet valve, a stationary optical window being fixed at a front end of the stationary pool body by a protection cover for the stationary optical window, a rear stop cover being fixed at a rear end of the stationary pool body; and a moveable pool body inserted into the stationary pool body, a moveable optical window being fixed at a front end of the moveable pool body by a protection cover for the moveable optical window, a pull-and-push handle being provided at a rear end of the moveable pool body.

As well, the infrared detection device can further include a gas outlet having a gas outlet valve coupled to the infrared detection device via a micro-air pump. The gas outlet can be located at the rear end of the stationary pool body. The protection cover for the moveable optical window can be provided with a gas discharge groove.

The disclosure also includes an infrared detection device for detecting coal mine polar gas, comprising: a central processor disposed within an outer casing, the central processor being electrically connected to a power supply, a light source, a detector, an alarm and indication lamp, an input and output module, a data collection and storage module, the power supply also being electrically connected to a power supply switch and a power supply interface, the input and output module also being connected to a computer communication interface, and the data collection and storage module also being electrically connected to the detector, and a gas pool assembly having a moveable optical window and fixed on the device is provided between the light source and the detector.

In some embodiments, the gas pool assembly having a moveable optical window comprises: a stationary pool body having a gas inlet with a gas inlet valve, a stationary optical window being fixed at a front end of the stationary pool body by a protection cover for the stationary optical window, a stopper being provided inside the stationary pool body, a rear stop cover being fixed at a rear end of the stationary pool body; and a moveable pool body inserted into the stationary pool body, a moveable optical window being fixed at a front end of the moveable pool body by the protection cover for the moveable optical window, a stop block being fixed at a rear end of the moveable pool body, an inside-pool stop sensor and an outside-pool stop sensor being fixed at both sides of the rear stop cover, a rack having driving threads being fixed at a bottom end of the moveable pool body, a rack position-control groove being provided at a bottom portion of the rear stop cover, a driving gear driven by a driving motor being provided at a bottom end of the gas pool, the central processor being electrically connected to the inside-pool stop sensor and the outside-pool stop sensor of the gas pool assembly having a moveable optical window, the central processor further being electrically connected to an electrical plug valve for gas inlet and the driving motor.

In some embodiments, the infrared detection device further includes a gas outlet having an electrical plug valve for gas outlet connected to the device via a micro-air pump. The gas outlet can be located at the rear end of the stationary pool body so as to continuously detect the gas. The central processor can be electrically connected to the electrical plug valve for gas outlet.

The infrared detection device can further include a rear stop cover fixed to the stationary pool body by a snap-fit of an inward-projection lock catch of a rear stop cover and an outward-projection lock catch of the stationary pool body. In some embodiments, the protection cover for the moveable optical window is provided with a gas discharge groove.

The disclosure also includes an infrared detection device for detecting coal mine polar gas, comprising: a central processor disposed within an outer casing, the central processor being electrically connected to a power supply, a light source, a detector, an alarm and indication lamp, an input and output module, a data collection and storage module, the power supply also being electrically connected to a power supply switch and a power supply interface, the input and output module also being connected to a computer communication interface, and the data collection and storage module also being electrically connected to the detector, a gas pool assembly having a moveable optical window and fixed on the device is provided between the light source and the detector.

In some embodiments, the gas pool assembly having a moveable optical window comprises: a stationary pool body having a gas inlet with an electrical plug valve for gas inlet and a gas outlet with an electrical plug valve for gas outlet, a second electrical three-way valve and a first electrical three-way valve being tube-connected between the gas inlet and the electrical plug valve for gas inlet, a third electrical three-way valve, a micro-air pump and a fourth electrical three-way valve being tube-connected between the gas outlet and the electrical plug valve for gas outlet, the fourth electrical three-way valve being tube-connected to the second electrical three-way valve, the first electrical three-way valve being tube-connected to the third electrical three-way valve, a stationary optical window being fixed at a front end of the stationary pool body by a protection cover for the stationary optical window, a stopper and an inside-pool stop sensor as well as an outside-pool stop sensor being provided inside the stationary pool body, a rear stop cover being fixed at a rear end of the stationary pool body, the protection cover for the moveable optical window for fixing a moveable optical window and a circular bracket thereon being placed inside the stationary pool body. As well, in some embodiments, the protection cover for the moveable optical window is provided with a gas discharge groove.

As well, the disclosure also includes a method of detecting coal mine polar gas using an infrared detection device comprising: a central processor disposed with an outer casing, the central processor being electrically connected to a power supply, a light source, a detector, an alarm and indication lamp, an input and output module, a data collection and storage module, the power supply also being electrically connected to a power supply switch and a power supply interface, the input and output module also being connected to a computer communication interface, and the data collection and storage module also being electrically connected to the detector, and a gas pool assembly having a moveable optical window and fixed on the device is provided between the light source and the detector.

In some embodiments, the gas pool assembly having a moveable optical window comprises: a stationary pool body having a gas inlet with a gas inlet valve, a stationary optical window being fixed at a front end of the stationary pool body by a protection cover for the stationary optical window, a rear stop cover being fixed at a rear end of the stationary pool body; and a moveable pool body inserted into the stationary pool body, a moveable optical window being fixed at a front end of the moveable pool body by a protection cover for the moveable optical window, a pull-and-push handle being provided at a rear end of the moveable pool body.

Methods can include, during a period of hand sampling for detecting: opening a gas inlet valve and pushing a pull-and-push handle until a protection cover for the moveable optical window comes into contact with a stationary optical window. After connecting a gas bag filled with gas to be detected to a gas inlet, methods can include pulling the pull-and-push handle until the protection cover for the moveable optical window comes into contact with a rear stop cover so as to at least partially fill the stationary pool body with the gas to be detected. As well, methods can include closing the gas inlet valve and scanning spectrum of the gas to be detected so as to analyze the gas to be detected.

Even still, the disclosure includes a method for detecting coal mine polar gas using an infrared detection device comprising: a central processor disposed with an outer casing, the central processor being electrically connected to a power supply, a light source, a detector, an alarm and indication lamp, an input and output module, a data collection and storage module, the power supply also being electrically connected to a power supply switch and a power supply interface, the input and output module also being connected to a computer communication interface, and the data collection and storage module also being electrically connected to the detector, and a gas pool assembly having a moveable optical window and fixed on the device is provided between the light source and the detector.

In some embodiments, the gas pool assembly having a moveable optical window comprises: a stationary pool body having a gas inlet with a gas inlet valve, a stationary optical window being fixed at a front end of the stationary pool body by a protection cover for the stationary optical window, a rear stop cover being fixed at a rear end of the stationary pool body; and a moveable pool body inserted into the stationary pool body, a moveable optical window being fixed at a front end of the moveable pool body by a protection cover for the moveable optical window, a pull-and-push handle being provided at a rear end of the moveable pool body; the infrared detection device comprising a gas outlet having a gas outlet valve coupled to the infrared detection device via a micro-air pump, wherein the gas outlet is located at the rear end of the stationary pool body.

Methods can include, during a period of continuous sampling: pumping out gas in lines using a micro-air pump until the lines are at least partially filled by gas to be detected; closing valves in the lines; opening a gas inlet valve; and pushing a pull-and-push handle until a protection cover for the moveable optical window comes into contact with a stationary optical window. After connecting the lines for gas to be detected to a gas inlet, methods can include opening valves in the lines; pulling the pull-and-push handle until the protection cover for the moveable optical window comes into contact with a rear stop cover so as to at least partially fill the stationary pool body with the gas to be detected; opening a gas outlet valve; and continuously pumping and circulating the gas to be detected using the micro-air pump and continuously scanning spectrum of the gas to be detected so as to analyze the gas to be detected.

Furthermore, the disclosure includes a method for detecting coal mine polar gas using an infrared detection device, comprising: a central processor disposed within an outer casing, the central processor being electrically connected to a power supply, a light source, a detector, an alarm and indication lamp, an input and output module, a data collection and storage module, the power supply also being electrically connected to a power supply switch and a power supply interface, the input and output module also being connected to a computer communication interface, and the data collection and storage module also being electrically connected to the detector, and a gas pool assembly having a moveable optical window and fixed on the device is provided between the light source and the detector.

In some embodiments, the gas pool assembly having a moveable optical window comprises: a stationary pool body having a gas inlet with a gas inlet valve, a stationary optical window being fixed at a front end of the stationary pool body by a protection cover for the stationary optical window, a stopper being provided inside the stationary pool body, a rear stop cover being fixed at a rear end of the stationary pool body; and a moveable pool body inserted into the stationary pool body, a moveable optical window being fixed at a front end of the moveable pool body by a protection cover for the moveable optical window, a stop block being fixed at a rear end of the moveable pool body, an inside-pool stop sensor and an outside-pool stop sensor being fixed at both sides of the rear stop cover, a rack having driving threads being fixed at a bottom end of the moveable pool body, a rack position-control groove being provided at a bottom portion of the rear stop cover, a driving gear driven by a driving motor being provided at a bottom end of the gas pool, the central processor being electrically connected to the inside-pool stop sensor and the outside-pool stop sensor of the gas pool assembly having a moveable optical window, the central processor further being electrically connected to an electrical plug valve for gas inlet and the driving motor.

Methods can include, during a period of hand sampling for detecting: causing, by a computer connected with a computer communication interface, an electrical plug valve for gas inlet to open and causing a driving motor to start; and pushing, by the driving motor, a moveable pool body until a stop block fixed at rear end of the moveable pool body contacts an outside-pool stop sensor. After connecting a gas bag filled with gas to be detected to a gas inlet, methods can include reversing the driving motor such that the driving motor works to pull the moveable pool body until a protection cover for the moveable optical window comes into contact with an inside-pool stop sensor so as to at least partially fill the stationary pool body with the gas to be detected; and closing the electrical plug valve for gas inlet and scanning spectrum of the gas to be detected so as to analyze the gas to be detected.

The disclosure also includes a method for detecting coal mine polar gas using an infrared detection device, comprising: a central processor disposed within an outer casing, the central processor being electrically connected to a power supply, a light source, a detector, an alarm and indication lamp, an input and output module, a data collection and storage module, the power supply also being electrically connected to a power supply switch and a power supply interface, the input and output module also being connected to a computer communication interface, and the data collection and storage module also being electrically connected to the detector, and a gas pool assembly having a moveable optical window and fixed on the device is provided between the light source and the detector. In some embodiments, the gas pool assembly having a moveable optical window comprises: a stationary pool body having a gas inlet with a gas inlet valve, a stationary optical window being fixed at a front end of the stationary pool body by a protection cover for the stationary optical window, a stopper being provided inside the stationary pool body, a rear stop cover being fixed at a rear end of the stationary pool body; and a moveable pool body inserted into the stationary pool body, a moveable optical window being fixed at a front end of the moveable pool body by a protection cover for the moveable optical window, a stop block being fixed at a rear end of the moveable pool body, an inside-pool stop sensor and an outside-pool stop sensor being fixed at both sides of the rear stop cover, a rack having driving threads being fixed at a bottom end of the moveable pool body, a rack position-control groove being provided at a bottom portion of the rear stop cover, a driving gear driven by a driving motor being provided at a bottom end of the gas pool.

In some embodiments, the central processor is electrically connected to the inside-pool stop sensor and the outside-pool stop sensor of the gas pool assembly having a moveable optical window. The central processor can also be electrically connected to an electrical plug valve for gas inlet and the driving motor. The infrared detection device can also comprise a gas outlet having an electrical plug valve for gas outlet connected to the device via a micro-air pump. The gas outlet can be located at the rear end of the stationary pool body so as to continuously detect the gas. The central processor can be electrically connected to the electrical plug valve for gas outlet.

Methods can include, during a period of continuous sampling: pumping out gas in lines using a micro-air pump until the lines are at least partially filled by gas to be detected; closing valves in the lines; causing, by a computer connected with a computer communication interface, an electrical plug valve for gas inlet to open and causing a driving motor to start; and pushing, by the driving motor, a moveable pool body until a stop block fixed at rear end of the moveable pool body contacts an outside-pool stop sensor. After connecting the lines for gas to be detected to a gas inlet, methods can include opening valves in the lines; pulling, by the driving motor, the moveable pool body until the protection cover for the moveable optical window comes into contact with an inside-pool stop sensor so as to at least partially fill the stationary pool body with the gas to be detected; opening an electrical plug valve for gas outlet; and continuously pumping and circulating the gas to be detected using the micro-air pump and continuously scanning spectrum of the gas to be detected so as to analyze the gas.

Even still, the disclosure includes a method for detecting coal mine polar gas using an infrared detection device for detecting coal mine polar gas, comprising: a central processor disposed within an outer casing, the central processor being electrically connected to a power supply, a light source, a detector, an alarm and indication lamp, an input and output module, a data collection and storage module, the power supply also being electrically connected to a power supply switch and a power supply interface, the input and output module also being connected to a computer communication interface, and the data collection and storage module also being electrically connected to the detector, a gas pool assembly having a moveable optical window and fixed on the device is provided between the light source and the detector.

In some embodiments, the gas pool assembly having a moveable optical window comprises: a stationary pool body having a gas inlet with an electrical plug valve for gas inlet and a gas outlet with an electrical plug valve for gas outlet, a second electrical three-way valve and a first electrical three-way valve being tube-connected between the gas inlet and the electrical plug valve for gas inlet, a third electrical three-way valve, a micro-air pump and a fourth electrical three-way valve being tube-connected between the gas outlet and the electrical plug valve for gas outlet, the fourth electrical three-way valve being tube-connected to the second electrical three-way valve, the first electrical three-way valve being tube-connected to the third electrical three-way valve, a stationary optical window being fixed at a front end of the stationary pool body by a protection cover for the stationary optical window, a stopper and an inside-pool stop sensor as well as an outside-pool stop sensor being provided inside the stationary pool body, a rear stop cover being fixed at a rear end of the stationary pool body, a protection cover for the moveable optical window for fixing a moveable optical window and a circular bracket thereon being placed inside the stationary pool body.

Methods can include, during a period of hand sampling for detecting: causing, by a computer connected with a computer communication interface, an electrical plug valve for gas inlet to open and sequentially open a second electrical three-way valve, a first electrical three-way valve, a third electrical three-way valve and a fourth electrical three-way valve in lines and then start a micro-air pump. Methods can also include pumping out gas inside a stationary pool body until a protection cover for the moveable optical window contacts an inside-pool front end stop sensor. After connecting a gas bag filled with gas to be detected to a gas inlet, methods can include causing, by the computer connected with a computer communication interface, to sequentially open a first electrical three-way valve, a third electrical three-way valve, a fourth electrical three-way valve and a second electrical three-way valve in lines and start the micro-air pump; pumping gas to be detected into the stationary pool body until the protection cover for the moveable optical window contacts an inside-pool rear end stop sensor so as to at least partially fill the stationary pool body with the gas to be detected; and closing the electrical plug valve for gas inlet and scanning spectrum of the gas to be detected so as to analyze the gas.

As well, during a period of continuous sampling, methods can include: pumping out gas in lines using a micro-air pump until the lines are at least partially filled by gas to be detected; closing valves in the lines; and causing, by a computer connected with a computer communication interface, an electrical plug valve for gas inlet to open and sequentially open a second electrical three-way valve, a first electrical three-way valve, a third electrical three-way valve and a fourth electrical three-way valve in lines and then to start a micro-air pump. Methods can include pumping out gas inside a stationary pool body until a protection cover for the moveable optical window comes into contact with an inside-pool front end stop sensor. After connecting the lines for gas to be detected to a gas inlet, methods can include: opening the valves in the lines, methods can include causing, by a computer connected with a computer communication interface, to sequentially open a first electrical three-way valve, a third electrical three-way valve, a fourth electrical three-way valve, and a second electrical three-way valve in lines and to start the micro-air pump. Methods can also include: pumping gas to be detected into the stationary pool body until the protection cover for the moveable optical window comes into contact with an inside-pool rear end stop sensor so as to at least partially fill the stationary pool body with the gas to be detected; opening an electrical plug valve for gas outlet; and continuously pumping and circulating the gas to be detected using the micro-air pump and continuously scanning spectrum of the gas to be detected so as to analyze the gas to be detected.

Some advantages of the present invention can be: a gas pool assembly having moveable optical window are fixed on the device and provided between the light source and the detector of the infrared detection device for coal mine polar gas, such that there is provided a structure to manually or automatically clean the gas in a gas pool in the manner of vacuum. In combination with the method for detecting coal mine polar gas using the infrared detection device for coal mine polar gas, the function of manually or automatically cleaning the gas in a gas pool in the manner of vacuum is realized, thereby may save $N_2$ gas used for cleaning, may reduce the cost of cleaning gas, may simplify the process of cleaning gas, may eliminate the error caused by the person, may ensure the reality of the spectrum of gas to be detected, may ensure the accuracy of the analysis for gas to be detected. Thus, it can provide reliable evidence for forecasting the fire disaster and conducting the rescue. The present invention is also applicable to other industrial fields.

The embodiments described above include many optional features and aspects. Features and aspects of the embodiments can be combined.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments. The above and other features of the present invention will become more apparent by describing in detail exemplary embodiments thereof with reference to the accompanying drawings, in which.

DETAILED DESCRIPTION

Figure 1:
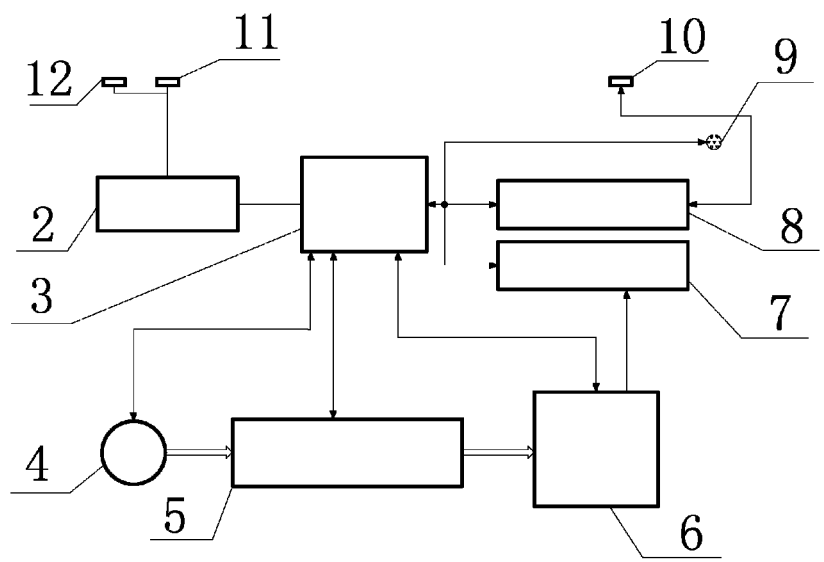
FIG. 1 is a structural schematic view of the present invention.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

LIST OF REFERENCE NUMERALS

Figure 2:
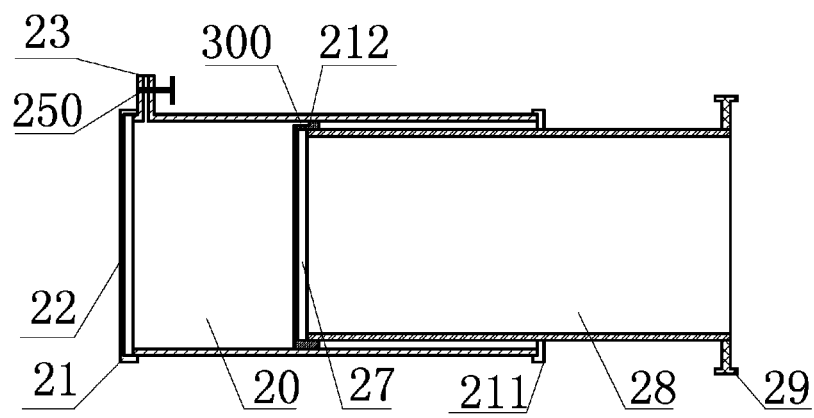
FIG. 2 is a structural schematic view of a first embodiment of the present invention.

2—Power supply
3—Central processor
4—Light source
5—Gas pool assembly with a moveable optical window
6—Detector
7—Data collection and storage module
8—Input and output module
9—Alarm and indication lamp
10—Computer communication interface
11—Power supply switch
12—Power supply interface
20—Stationary pool body
21—Stationary optical window
22—Protection cover for stationary optical window
23—Gas inlet
24—Gas outlet
25—Electrical plug valve (stopcock) for gas inlet
26—Micro-air pump
27—Moveable optical window
28—Moveable pool body
29—Pull-and-push handle
30—Stopper
31—Driving motor
32—Driving gear
33—Driving threads
34—Inside-pool stop sensor
35—Fourth electrical three-way valve
36—Rack position-control groove
38—Circular bracket
134—Front end stop sensor
211—Rear stop cover
212—Protection cover for moveable optical window
250—Gas inlet valve
251—Electrical plug valve (stopcock) for gas outlet
300—Gas discharge groove
341—Outside-pool stop sensor
342—Stop block
351—First electrical three-way valve
352—Second electrical three-way valve
353—Third electrical three-way valve
400—Inward-projection lock catch of rear stop cover
401—Outward-projection lock catch of stationary pool body
1341—Rear end stop sensor
2501—Gas outlet valve Infrared Detection Device Embodiments Referring to FIGS. 1 and 2, an infrared detection device for detecting coal mine polar gas can comprise a central processor 3 located within an outer casing. The central processor 3 can also be electrically connected to a power supply 2, a light source 4, a detector 6, an alarm and indication lamp 9, an input and output module 8, a data collection and storage module 7. The power supply 2 can also be electrically connected to a power supply switch 11 and a power supply interface 12. Moreover, the input and output module 8 can also be connected to a computer communication interface 10, and the data collection and storage module 7 can also be electrically connected to the detector 6.

A gas pool assembly 5 can have a moveable optical window provided between the light source 4 and the detector 6. Accordingly, the gas pool assembly 5 can have a moveable optical window that can comprise: a stationary pool body 20 having a gas inlet 23 with a gas inlet valve 250, a stationary optical window 21 being fixed at a front end of the stationary pool body 20 by a protection cover for the stationary optical window 22, and a rear stop cover 211 being fixed at a rear end of the stationary pool body 20. As well, the gas pool assembly 5 can have a moveable pool body 28 inserted into the stationary pool body 20, a moveable optical window 27 being fixed at a front end of the moveable pool body 28 by a protection cover for the moveable optical window 212, a pull-and-push handle 29 being provided at a rear end of the moveable pool body 28. As well, the protection cover for the moveable optical window 212 can be provided with a gas discharge groove 300.

Figure 3:
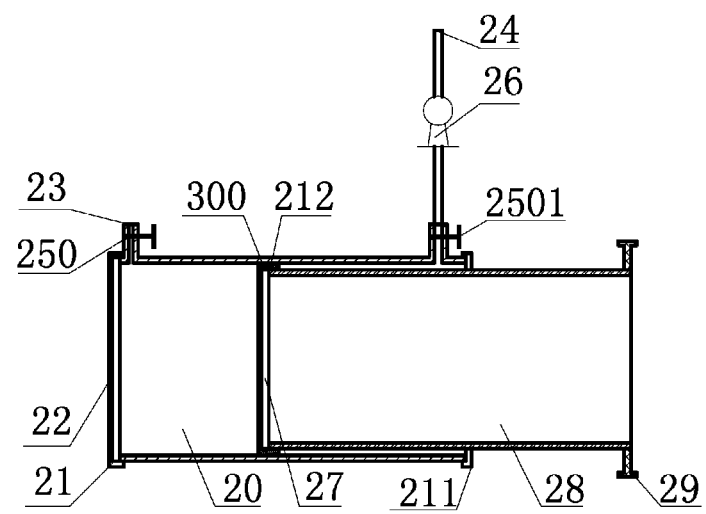
FIG. 3 is a structural schematic view of a second embodiment of the present invention.

Referring now to FIGS. 1 and 3, an infrared detection device for detecting coal mine polar gas can comprise a central processor 3 located within an outer casing. The central processor 3 can be electrically connected to a power supply 2, a light source 4, a detector 6, an alarm and indication lamp 9, an input and output module 8, a data collection and storage module 7. As well, the power supply 2 can also be electrically connected to a power supply switch 11 and a power supply interface 12. Even still, the input and output module 8 can also be connected to a computer communication interface 10. Furthermore, the data collection and storage module 7 can also be electrically connected to the detector 6.

A gas pool assembly 5 can have a moveable optical window and fixed on the device can be provided between the light source 4 and the detector 6. Accordingly, the gas pool assembly 5 can have a moveable optical window that can comprise: a stationary pool body 20 having a gas inlet 23 with a gas inlet valve 250, a stationary optical window 21 being fixed at a front end of the stationary pool body 20 by a protection cover for the stationary optical window 22, and a rear stop cover 211 being fixed at a rear end of the stationary pool body 20. As well, the gas pool assembly 5 can include a moveable pool body 28 inserted into the stationary pool body 20, a moveable optical window 27 being fixed at a front end of the moveable pool body 28 by a protection cover for the moveable optical window 212, and a pull-and-push handle 29 being provided at a rear end of the moveable pool body 28.

A gas outlet 24 having a gas outlet valve 2501 connected thereto via a micro-air pump 26 can be provided at the rear end of the stationary pool body 20 so as to continuously detect the gas to be detected. As well, the protection cover for the moveable optical window 212 can be provided with a gas discharge groove 300.

With reference to FIGS. 1, 4, 7 and 8, an infrared detection device for coal mine polar gas can include a central processor 3 located within an outer casing. The central processor 3 can be electrically connected to a power supply 2, a light source 4, a detector 6, an alarm and indication lamp 9, and an input and output module 8, a data collection and storage module 7. The power supply 2 can also be electrically connected to a power supply switch 11 and a power supply interface 12. As well, the input and output module 8 can also be connected to a computer communication interface 10. The data collection and storage module 7 can also be electrically connected to the detector 6.

A gas pool assembly 5 can have a moveable optical window and fixed on the device can be provided between the light source 4 and the detector 6. Accordingly, the gas pool assembly 5 can have a moveable optical window that can comprise: a stationary pool body 20 having a gas inlet 23 with a gas inlet valve 250, a stationary optical window 21 being fixed at a front end of the stationary pool body 20 by a protection cover for the stationary optical window 22, a stopper 30 being provided inside the stationary pool body 20, and a rear stop cover 211 being fixed at a rear end of the stationary pool body 20. The gas pool assembly 5 can include a moveable pool body 28 inserted into the stationary pool body 20, a moveable optical window 27 being fixed at a front end of the moveable pool body 28 by a protection cover for the moveable optical window 212, a stop block 342 being fixed at a rear end of the moveable pool body 28, an inside-pool stop sensor 34 and an outside-pool stop sensor 341 being fixed at both sides of the rear stop cover 211, a rack having driving threads 33 being fixed at a bottom end of the moveable pool body 28, a rack position-control groove 36 being provided at a bottom portion of the rear stop cover 211, and a driving gear 32 driven by a driving motor 31 being provided at a bottom end of the gas pool. The central processor 3 can be electrically connected to the inside-pool stop sensor 34 and the outside-pool stop sensor 341 of the gas pool assembly 5 having a moveable optical window. As well, the central processor 3 can be electrically connected to the electrical plug valve for gas inlet 25 and the driving motor 31.

The infrared detection device can include a rear stop cover 211 fixed at the stationary pool body 20 by the snap-fit of an inward-projection lock catch of rear stop cover 400 and an outward-projection lock catch of stationary pool body 40. The protection cover for the moveable optical window 212 can be provided with a gas discharge groove 300.

Now referring to FIGS. 1, 5, 7 and 8, an infrared detection device for coal mine polar gas can comprise a central processor 3 located within an outer casing. The central processor 3 can be electrically connected to a power supply 2, a light source 4, a detector 6, an alarm and indication lamp 9, an input and output module 8, and a data collection and storage module 7. The power supply 2 can also be electrically connected to a power supply switch 11 and a power supply interface 12. As well, the input and output module 8 can also be connected to a computer communication interface 10. The data collection and storage module 7 can also be electrically connected to the detector 6.

A gas pool assembly 5 can have a moveable optical window provided between the light source 4 and the detector 6. The gas pool assembly 5 having the moveable optical window can include a stationary pool body 20 having a gas inlet 23 with a gas inlet valve 250, a stationary optical window 21 being fixed at a front end of the stationary pool body 20 by a protection cover for the stationary optical window 22, a stopper 30 being provided inside the stationary pool body 20, a rear stop cover 211 being fixed at a rear end of the stationary pool body 20; and a moveable pool body 28 inserted into the stationary pool body 20. As well, the moveable optical window 27 can be fixed at a front end of the moveable pool body 28 by a protection cover for the moveable optical window 212. The gas pool assembly 5 can include a stop block 342 being fixed at a rear end of the moveable pool body 28, an inside-pool stop sensor 34 and an outside-pool stop sensor 341 being fixed at both sides of the rear stop cover 211, a rack having driving threads 33 being fixed at a bottom end of the moveable pool body 28, a rack position-control groove 36 being provided at a bottom portion of the rear stop cover 211, a driving gear 32 driven by a driving motor 31 being provided at a bottom end of the gas pool, the central processor 3 being electrically connected to the inside-pool stop sensor 34, the outside-pool stop sensor 341 of the gas pool assembly 5 having a moveable optical window. The central processor 3 can be electrically connected to the electrical plug valve for gas inlet 25 and the driving motor 31.

In such embodiments, a gas outlet 24 having an electrical plug valve for gas outlet 251 can be connected thereto via a micro-air pump 26 provided at the rear end of the stationary pool body 20 so as to continuously detect the gas to be detected. As well, the central processor 3 can be electrically connected to the electrical plug valve for gas outlet 251. A rear stop cover 211 can be fixed at the stationary pool body 20 by the snap-fit of an inward-projection lock catch of rear stop cover 400 and an outward-projection lock catch of stationary pool body 401. The protection cover for the moveable optical window 212 can be provided with a gas discharge groove 300.

Figure 6:
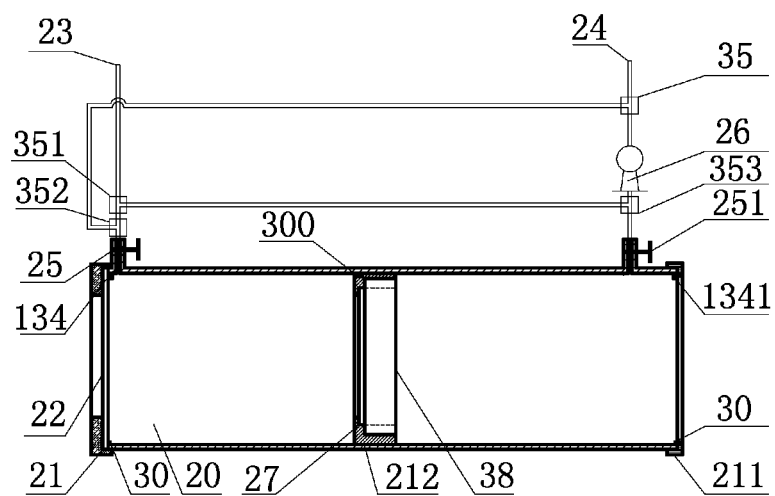
FIG. 6 is a structural schematic view of a fifth embodiment of the present invention.
Figure 7:
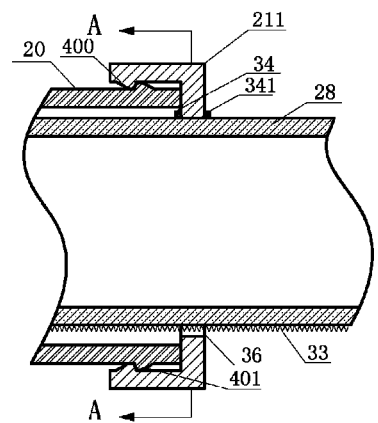
FIG. 7 is a local structural schematic view of FIG. 4 or FIG. 5 of the present invention.
Figure 8:
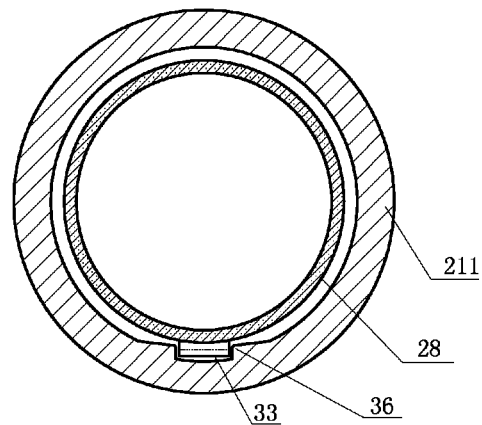
FIG. 8 is a cross-section view of the local structural schematic view of FIG. 4 or FIG. 5 of the present invention.

FIGS. 1 and 6 illustrate an infrared detection device for coal mine polar gas, comprising: a central processor 3 inside an outer casing, the central processor 3 being electrically connected to a power supply 2, a light source 4, a detector 6, an alarm and indication lamp 9, an input and output module 8, a data collection and storage module 7, the power supply 2 also being electrically connected to a power supply switch 11 and a power supply interface 12, the input and output module 8 also being connected to a computer communication interface 10, and the data collection and storage module 7 also being electrically connected to the detector 6. The infrared detection device can also include a gas pool assembly 5 having a moveable optical window. The gas pool assembly 5 can be fixed on the infrared detection device between the light source 4 and the detector 6.

In such embodiments, the gas pool assembly 5 having a moveable optical window comprises: a stationary pool body 20 having a gas inlet 23 with an electrical plug valve for gas inlet 25 and a gas outlet 24 with an electrical plug valve for gas outlet 251, a second electrical three-way valve 352 and a first electrical three-way valve 351 being tube-connected between the gas inlet 23 and the electrical plug valve for gas inlet 25, a third electrical three-way valve 353, a micro-air pump 26 and a fourth electrical three-way valve 35 being tube-connected between the gas outlet 24 and the electrical plug valve for gas outlet 251. The fourth electrical three-way valve 35 can be tube-connected to the second electrical three-way valve 352. The first electrical three-way valve 351 can be tube-connected to the third electrical three-way valve 353.

As well, the infrared detection device can include a stationary optical window 21 fixed at a front end of the stationary pool body 20 by a protection cover for the stationary optical window 22, a stopper 30 and an inside-pool stop sensor 34 as well as an outside-pool stop sensor 341 being provided inside the stationary pool body 20, a rear stop cover 211 being fixed at a rear end of the stationary pool body 20, a protection cover for the moveable optical window 212 for fixing a moveable optical window 27 and a circular bracket 38 thereon being placed inside the stationary pool body 20. In such embodiments, the protection cover for the moveable optical window 212 can be provided with a gas discharge groove 300.

Methods of Detecting Coal Mine Polar Gas

Figure 9:
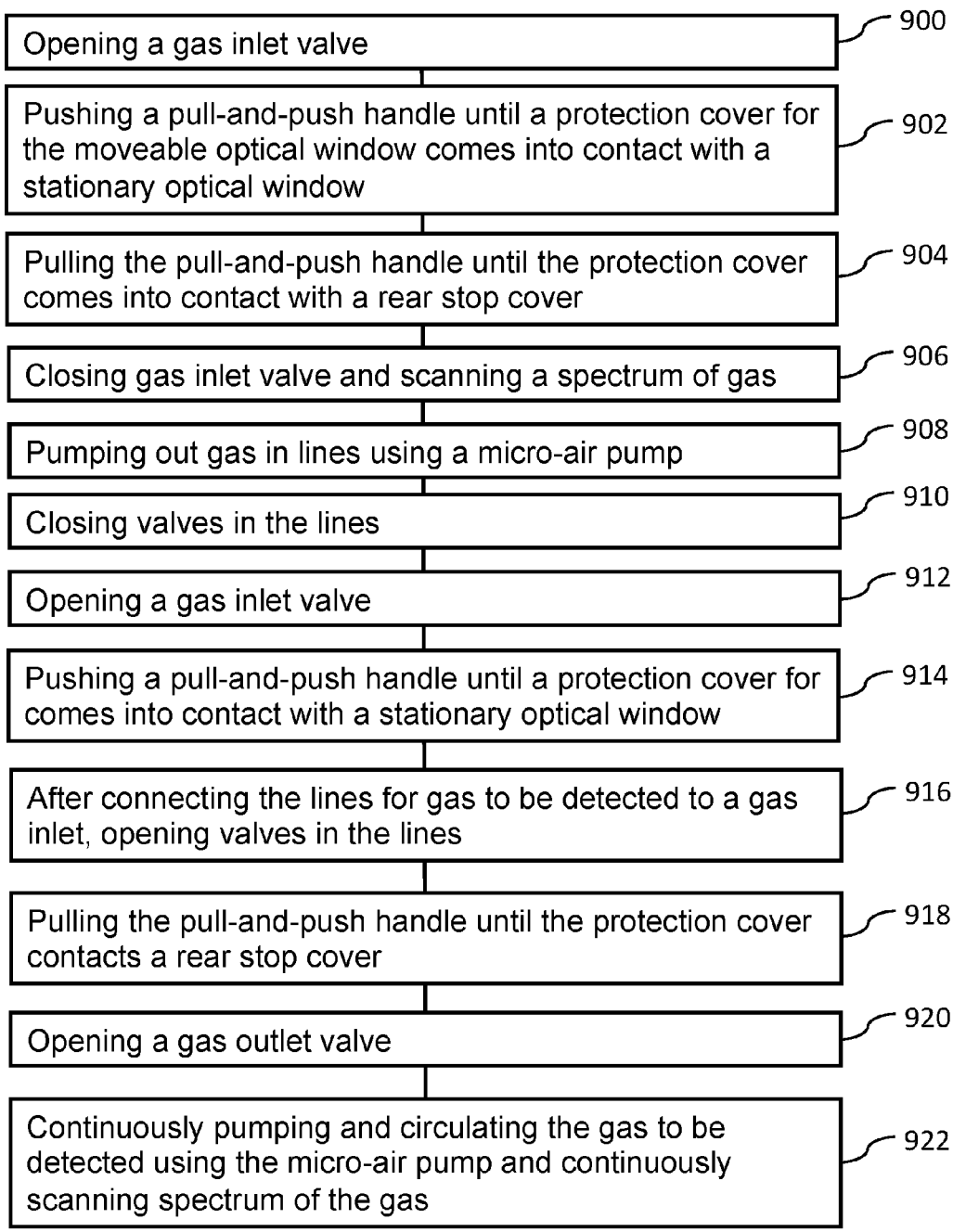
FIGS. 9, 10, 11a, and 11b depict flow diagrams showing methods of operating infrared detection devices, according to some embodiments.
Figure 10:
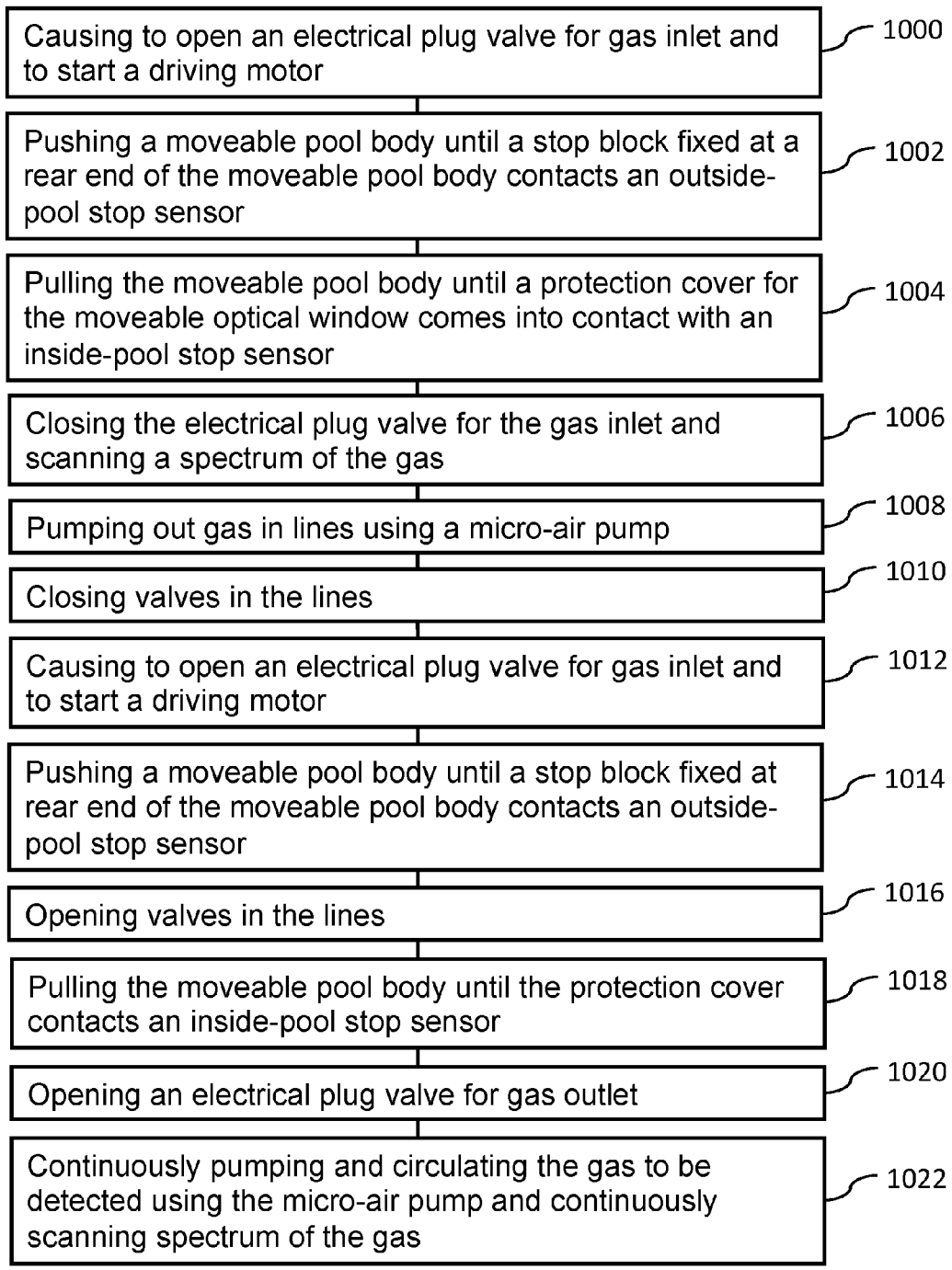
Figure 11A:
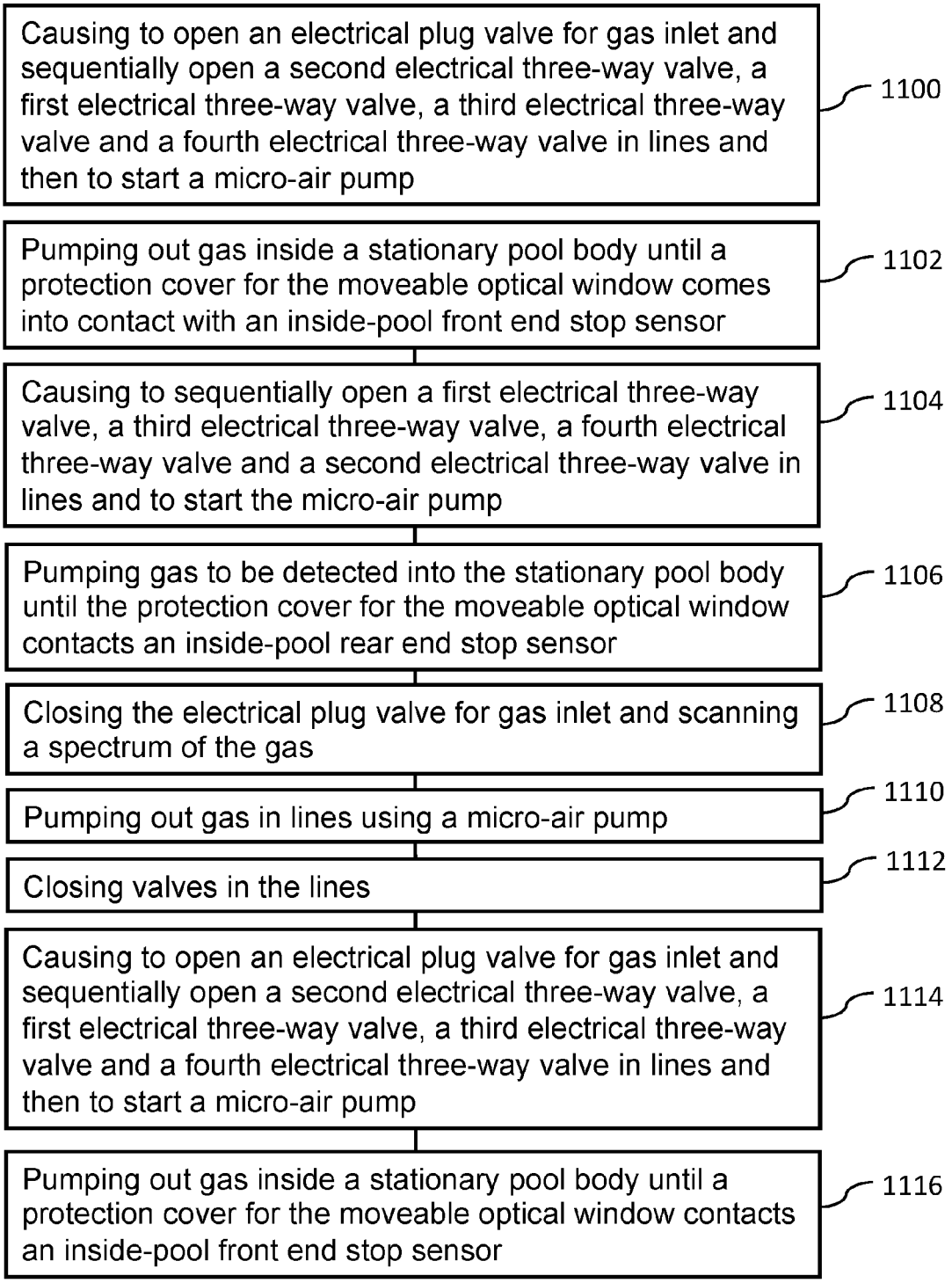
Figure 11B:
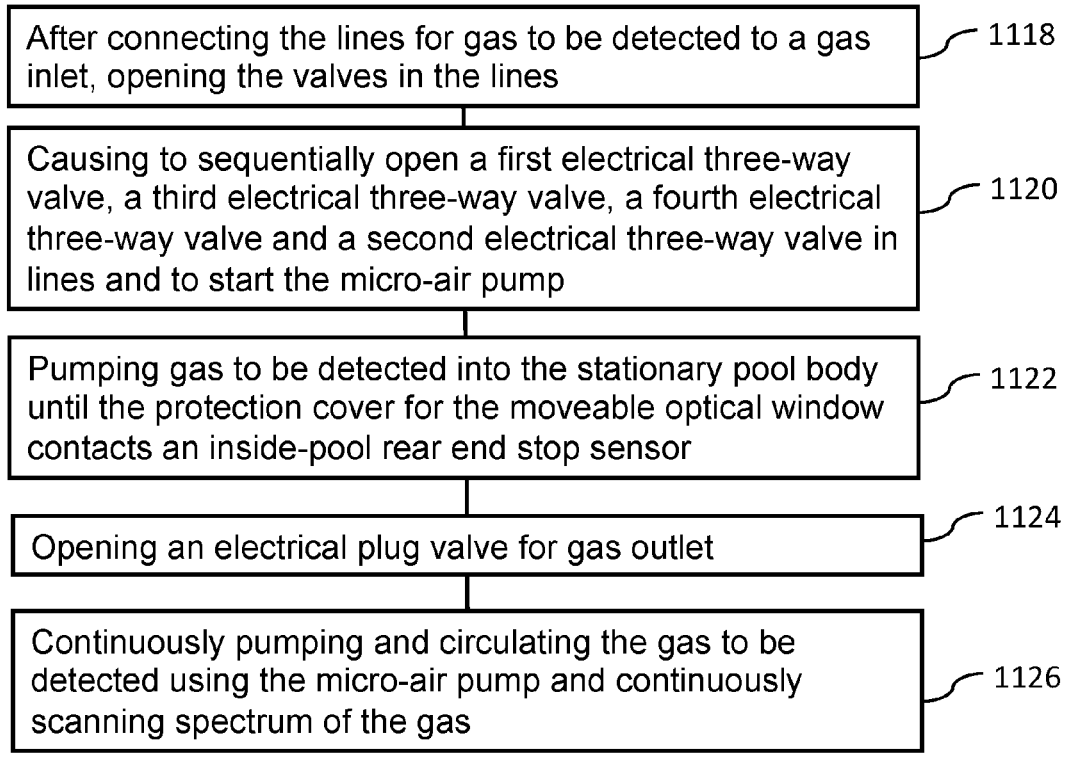

FIGS. 1, 2 and 3 illustrate an infrared detection device that can be used for detecting coal mine polar gas. As further shown in FIG. 9, during a period of hand sampling for detecting, methods can include opening a gas inlet valve 250 (at step 900); and pushing a pull-and-push handle 29 until a protection cover for the moveable optical window 212 comes into contact with a stationary optical window 21 (at step 902). After connecting a gas bag filled with gas to be detected to a gas inlet 23, methods can include pulling the pull-and-push handle 29 until the protection cover for the moveable optical window 212 comes into contact with a rear stop cover 211 so as to at least partially fill the stationary pool body 20 with the gas to be detected (at step 904). After connecting a gas bag filled with gas to be detected to a gas inlet 23, methods can include pulling the pull-and-push handle 29 until the protection cover for the moveable optical window 212 comes into contact with a rear stop cover 211 so as to fully fill the stationary pool body 20 with the gas to be detected.

Methods can also include closing the gas inlet valve 250 and scanning a spectrum of the gas to be detected so as to analyze the gas to be detected (at step 906). During a period of continuous sampling, methods can include pumping out gas in lines using a micro-air pump until the lines are at least partially filled by gas to be detected (at step 908). Some methods can include pumping out gas in lines using a micro-air pump until the lines are fully filled by gas to be detected.

Methods can also include closing valves in the lines (at step 910); opening a gas inlet valve 250 (at step 912); and pushing a pull-and-push handle 29 until a protection cover for the moveable optical window 212 comes into contact with a stationary optical window 21 (at step 914). After connecting the lines for gas to be detected to a gas inlet 23, methods can include opening valves in the lines (at step 916); pulling the pull-and-push handle 29 until the protection cover for the moveable optical window 212 comes into contact with a rear stop cover 211 so as to at least partially fill the stationary pool body 20 with the gas to be detected (at step 918). Methods can also include pulling the pull-and-push handle 29 until the protection cover for the moveable optical window 212 comes into contact with a rear stop cover 211 so as to fully fill the stationary pool body 20 with the gas to be detected.

Even still, methods can include opening a gas outlet valve 2501 (at step 920). As well, some methods can include continuously pumping and circulating the gas to be detected using the micro-air pump 26 and continuously scanning spectrum of the gas to be detected so as to analyze the gas to be detected (at step 922).

Figure 4:
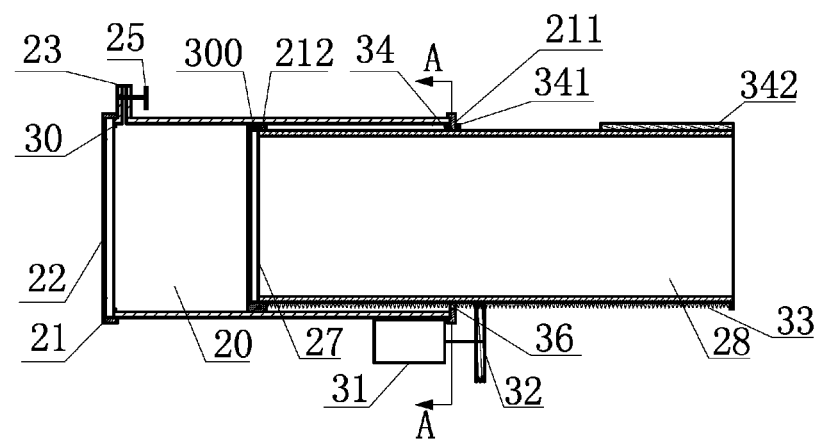
FIG. 4 is a structural schematic view of a third embodiment of the present invention.
Figure 5:
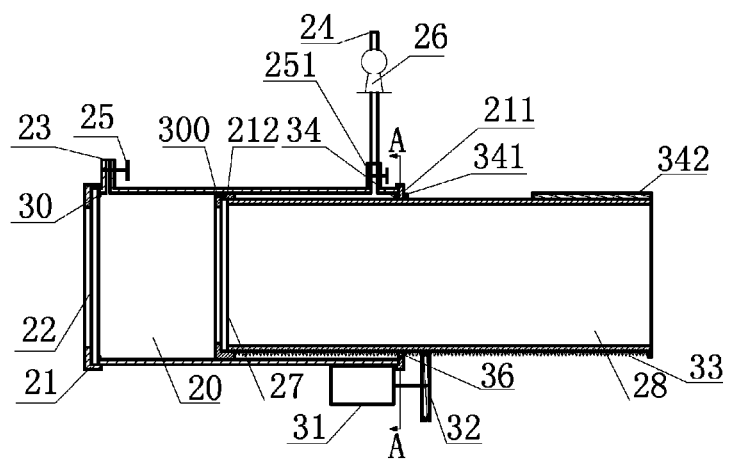
FIG. 5 is a structural schematic view of a fourth embodiment of the present invention.

Referring now to FIGS. 1, 4 and 5, a method for detecting coal mine polar gas using an infrared detection device for detecting coal mine polar gas can include, causing, by a computer connected with a computer communication interface 10, to open an electrical plug valve for gas inlet 25 and to start a driving motor 31 (at step 1000). Methods can also include pushing, by a driving motor 31, a moveable pool body 28 until a stop block 342 fixed at a rear end of the moveable pool body 28 contacts an outside-pool stop sensor 341 (at step 1002). It should be appreciated that the steps can occur during a period of hand sampling for detecting.

After connecting a gas bag filled with gas to be detected to a gas inlet 23, methods can include giving commands to reverse the driving motor 31 such that the driving motor 31 pulls the moveable pool body 28 until a protection cover for the moveable optical window 212 comes into contact with an inside-pool stop sensor 34 so as to at least partially fill the stationary pool body 20 with the gas to be detected (at step 1004). After connecting a gas bag filled with gas to be detected to a gas inlet 23, methods can include giving commands to reverse the driving motor 31 such that the driving motor 31 works to pull the moveable pool body 28 until a protection cover for the moveable optical window 212 comes into contact with an inside-pool stop sensor 34 so as to fully fill the stationary pool body 20 with the gas to be detected.

Methods can also include closing the electrical plug valve for gas inlet 25 and scanning spectrum of the gas to be detected so as to analyze the gas to be detected (at step 1006). During a period of continuous sampling, methods can include pumping out gas into lines using a micro-air pump until the lines are at least partially filled by gas to be detected (at step 1008). Methods can also include pumping out gas into lines using a micro-air pump until the lines are fully filled by gas to be detected.

Even still, methods can include closing valves in the lines (at step 1010); causing, by a computer connected with a computer communication interface 10, to open an electrical plug valve for gas inlet 25 and to start a driving motor 31 (at step 1012). As well, methods can include pushing, by the driving motor 31, a moveable pool body 28 until a stop block 342 fixed at a rear end of the moveable pool body 28 contacts an outside-pool stop sensor 341 (at step 1014).

After connecting the lines for gas to be detected to a gas inlet 23, methods can include opening valves in the lines (at step 1016). In some methods, the driving motor 31 can pull the moveable pool body 28 until the protection cover for the moveable optical window 212 comes into contact with an inside-pool stop sensor 34 so as to at least partially fill the stationary pool body 20 with the gas to be detected (at step 1018). In some methods, the driving motor 31 works to pull the moveable pool body 28 until the protection cover for the moveable optical window 212 comes into contact with an inside-pool stop sensor 34 so as to fully fill the stationary pool body 20 with the gas to be detected.

Methods can also include opening an electrical plug valve for gas outlet 251 (at step 1020). Even still, some methods can include continuously pumping and circulating the gas to be detected using the micro-air pump 26 and continuously scanning spectrum of the gas to be detected so as to analyze the gas to be detected (at step 1022).

Referring now to FIGS. 1 and 6, a method for detecting coal mine polar gas using an infrared detection device for detecting coal mine polar gas can include, during a period of hand sampling for detecting, causing, by a computer connected with a computer communication interface 10, to open an electrical plug valve for gas inlet 25 and sequentially open a second electrical three-way valve 352, a first electrical three-way valve 351, a third electrical three-way valve 353 and a fourth electrical three-way valve 35 in lines and then to start a micro-air pump 26 (at step 1100). Methods can also include pumping out gas inside a stationary pool body 20 until a protection cover for the moveable optical window 212 comes into contact with an inside-pool front end stop sensor 134 (at step 1102).

After connecting a gas bag filled with gas to be detected to a gas inlet 23, methods can include causing, by the computer connected with a computer communication interface 10, to sequentially open a first electrical three-way valve 351, a third electrical three-way valve 353, a fourth electrical three-way valve 35 and a second electrical three-way valve 352 in lines and to start the micro-air pump 26 (at step 1104). Methods can also include pumping gas to be detected into the stationary pool body 20 until the protection cover for the moveable optical window 212 contacts an inside-pool rear end stop sensor 1341 so as to at least partially fill the stationary pool body 20 with the gas to be detected (at step 1106). Methods can include pumping gas to be detected into the stationary pool body 20 until the protection cover for the moveable optical window 212 comes into contact with an inside-pool rear end stop sensor 1341 so as to fully fill the stationary pool body 20 with the gas to be detected.

Some methods include closing the electrical plug valve for gas inlet 25 and scanning spectrum of the gas to be detected so as to analyze the gas to be detected (at step 1108). During a period of continuous sampling, methods can include pumping out gas into lines using a micro-air pump until the lines are at least partially filled by gas to be detected (at step 1110). Methods can include pumping out gas into lines using a micro-air pump until the lines are fully filled by gas to be detected.

Methods can include closing valves in the lines (at step 1112) and causing, by a computer connected with a computer communication interface 10, to open an electrical plug valve for gas inlet 25 and sequentially open a second electrical three-way valve 352, a first electrical three-way valve 351, a third electrical three-way valve 353 and a fourth electrical three-way valve 35 in lines and then to start a micro-air pump 26 (at step 1114).

Methods may even include pumping out gas inside a stationary pool body 20 until a protection cover for the moveable optical window 212 contacts an inside-pool front end stop sensor 134 (at step 1116). After connecting the lines for gas to be detected to a gas inlet 23, methods can include opening the valves in the lines (at step 1118) and causing, by a computer connected with a computer communication interface 10, to sequentially open a first electrical three-way valve 351, a third electrical three-way valve 353, a fourth electrical three-way valve 35 and a second electrical three-way valve 352 in lines and to start the micro-air pump 26 (at step 1120).

Methods can include pumping gas to be detected into the stationary pool body 20 until the protection cover for the moveable optical window 212 contacts an inside-pool rear end stop sensor 1341 so as to at least partially fill the stationary pool body 20 with the gas to be detected (at step 1122). Methods can include pumping gas to be detected into the stationary pool body 20 until the protection cover for the moveable optical window 212 contacts an inside-pool rear end stop sensor 1341 so as to fully fill the stationary pool body 20 with the gas to be detected.

As well, some methods can include opening an electrical plug valve for gas outlet 251 (at step 1124). Even still, some methods can include continuously pumping and circulating the gas to be detected using the micro-air pump 26 and continuously scanning spectrum of the gas to be detected so as to analyze the gas to be detected (at step 1126).

Interpretation

None of the steps described herein is essential or indispensable. Any of the steps can be adjusted or modified.

Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

The following is claimed:

1. An infrared detection device for detecting coal mine polar gas, comprising:
   a stationary pool body having a gas inlet and a gas outlet;
   a stationary optical window coupled to the stationary pool body; and
   a moveable optical window moveably disposed inside the stationary pool body, wherein the moveable optical window moves with respect to the stationary pool body and in response to gas flowing through the gas inlet and the gas outlet.

2. The infrared detection device of claim 1, further comprising a protection cover for the stationary optical window that couples the stationary optical window to a front end of the stationary pool body.

3. The infrared detection device of claim 2, further comprising a stopper, an inside-pool stop sensor, and an outside-pool stop sensor located inside the stationary pool body.

4. The infrared detection device of claim 3, further comprising a protection cover for the moveable optical window and a circular bracket coupled inside the stationary pool body.

5. The infrared detection device of claim 4, wherein the protection cover for the moveable optical window is provided with a gas discharge groove.

6. The infrared detection device of claim 5, further comprising a rear stop cover coupled to a rear end of the stationary pool body.

7. The infrared detection device of claim 6, further comprising a rear stop sensor coupled to the rear end of the stationary pool body.

8. The infrared detection device of claim 7, further comprising a front stop sensor coupled to the front end of the stationary pool body.

9. The infrared detection device of claim 1, further comprising a first electrical three-way valve in fluid communication between the gas inlet and the gas outlet.

10. The infrared detection device of claim 9, further comprising a second electrical three-way valve in fluid communication between the first electrical three-way valve and the gas inlet.

11. The infrared detection device of claim 10, further comprising a third electrical three-way valve in fluid communication between the first electrical three-way valve and the gas outlet.

12. The infrared detection device of claim 11, further comprising a micro-air pump in fluid communication between the third electrical three-way valve and the second electrical three-way valve.

13. The infrared detection device of claim 12, further comprising a fourth electrical three-way valve in fluid communication between the micro-air pump and the second electrical three-way valve.

14. The infrared detection device of claim 13, wherein the moveable optical window moves along a first direction inside the stationary pool body when gas flows through the gas inlet, and the moveable optical window moves along a second direction inside the stationary pool body when gas flows through the gas outlet, wherein the second direction is opposite from the first direction.

15. The infrared detection device of claim 13, wherein the first electrical three-way valve, the second electrical three-way valve, the third electrical three-way valve, the fourth electrical three-way valve, and the micro-air pump are in fluid communication via tube-connections.

16. The infrared detection device of claim 13, further comprising an electrical plug valve for gas inlet and an electrical plug valve for gas outlet.

17. The infrared detection device of claim 13, wherein the stationary optical window is coupled to a front end of the stationary pool body.

18. The infrared detection device of claim 13, wherein the first electrical three-way valve and the second electrical three-way valve are located adjacent a front end of the stationary pool body.

19. The infrared detection device of claim 18, wherein the third electrical three-way valve, the fourth electrical three-way valve, and the micro-air pump are located adjacent a rear end of the stationary pool body.

20. The infrared detection device of claim 1, further comprising a central processor disposed with an outer casing, the central processor electrically coupled to a power supply, a light source, a detector, an alarm and indication lamp, an input and output module, a data collection and storage module, and a gas pool assembly having a moveable optical window, wherein the power supply is electrically coupled to a power supply switch and a power supply interface, the input and output module is coupled to a computer communication interface, the data collection and storage module is electrically coupled to the detector, and the gas pool assembly is located between the light source and the detector.

* * * * *